United States Patent [19]

Ashton

[11] Patent Number: Plant 5,273

[45] Date of Patent: Aug. 21, 1984

[54] SUGAR MAPLE NAMED FLAX MILL MAJESTY

[76] Inventor: Roger L. Ashton, Scotch Hill Rd., Cambridge, N.Y. 12816

[21] Appl. No.: 355,715

[22] Filed: Mar. 8, 1982

[51] Int. Cl.[3] ..... A01H 5/00

[52] U.S. Cl. ..... Plt./51

[58] Field of Search ..... Plt./51

*Primary Examiner*—Robert E. Bagwill

*Attorney, Agent, or Firm*—Wm. A. Snow

[57] ABSTRACT

This disclosure concerns a new and distinct variety of *Acer saccharum,* commonly known as sugar maple tree, characterized by a symmetrically shaped head at a very early age, not seen in the usual sugar maple tree, with a straight leader, an abundance of branches and a vigorous and hearty growth habit.

3 Drawing Figures

BACKGROUND OF THE INVENTION

This new variety of sugar maple tree was found growing in a bed of five hundred sugar maple trees at my nursery at Cambridge, N.Y. The trunk calipered as much as three-quarters to one inch a year. The tree grew balanced, had an extremely dense and nicely shaped ovoid crown at an early age, was a vigorous grower, survived 38° F. below zero without cracking, and had no sun scald problems. This tree has been propagated by budding at Moller's Nursery, Gresham, Oreg., and McGill & Son Nursery, Fairview, Oreg., and the second generation is disclosing the same characteristics as the parent tree and is growing faster than other seedling sugar maple trees and faster than their patented varieties.

SUMMARY OF THE INVENTION

A new and distinct cultivar of sugar maple tree characterized by its vigorous growth habit, dense crown, freedom from cracking, having survived in 38° F. below zero with no cracking, having no sun scald problems, and very large leaves.

DETAILED DESCRIPTION OF THE NEW PLANT VARIETY

Figure 1:
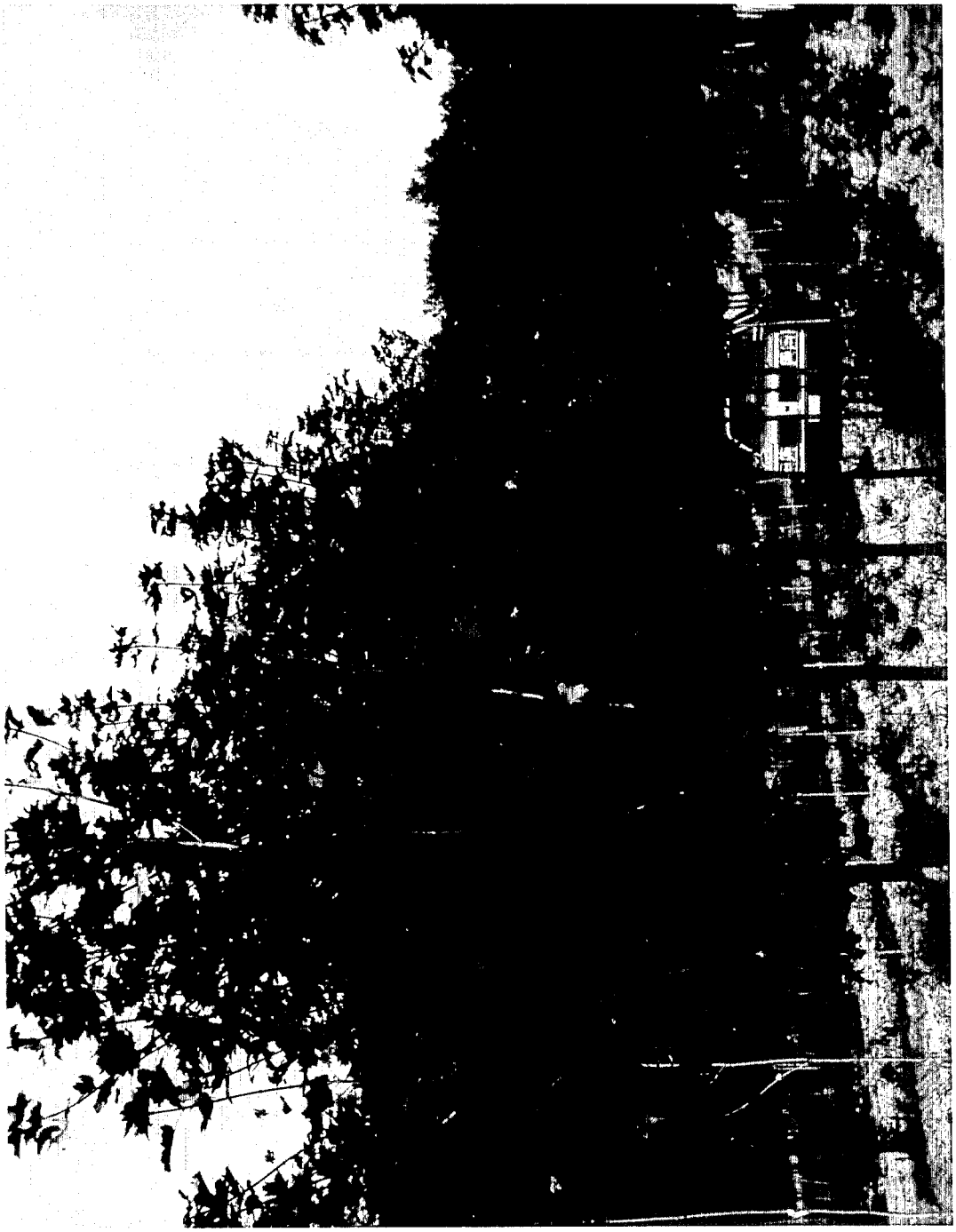
FIG. 1 is a photograph of a stand of my new variety.
Figure 2:
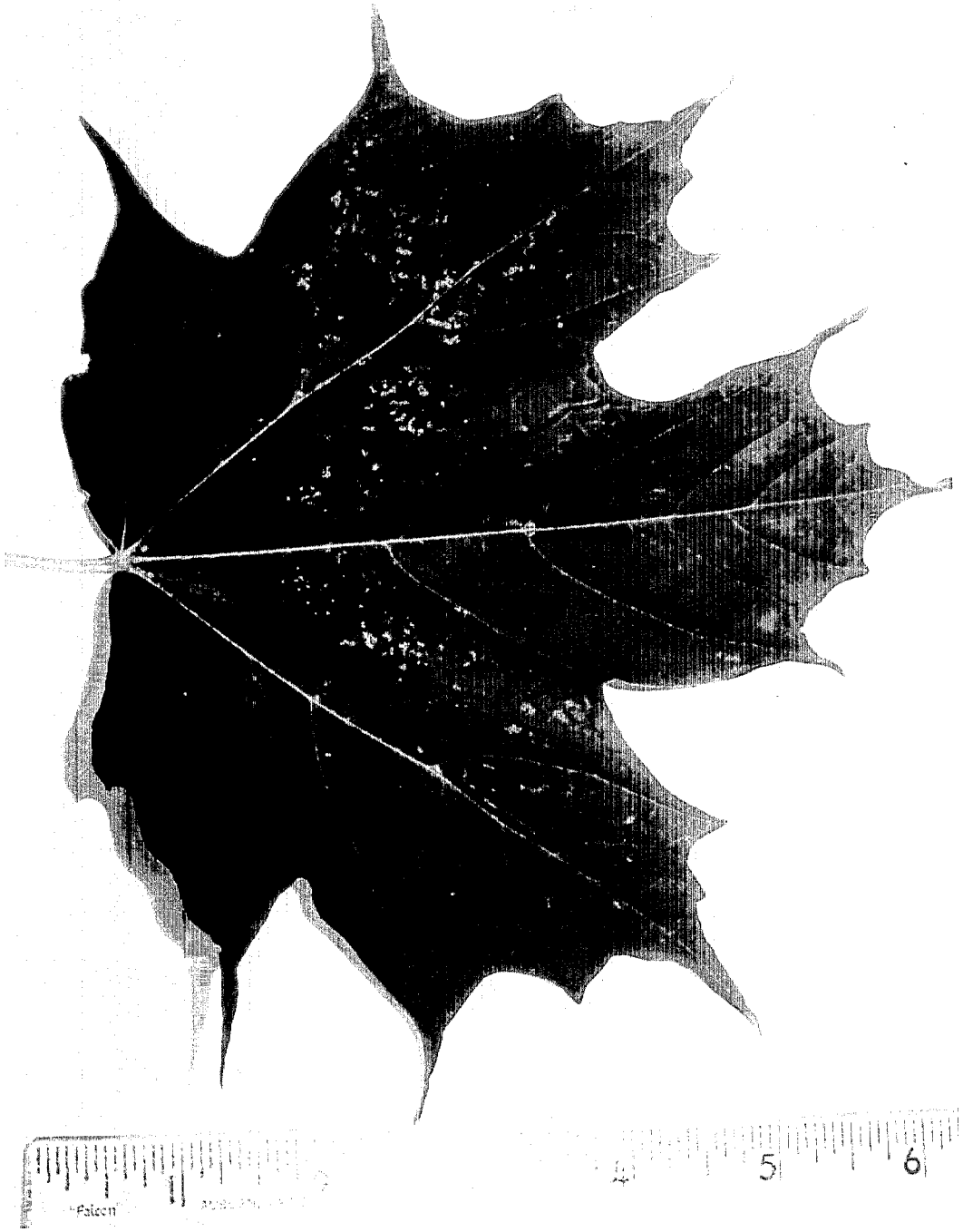
FIG. 2 is a photograph showing one leaf.
Figure 3:
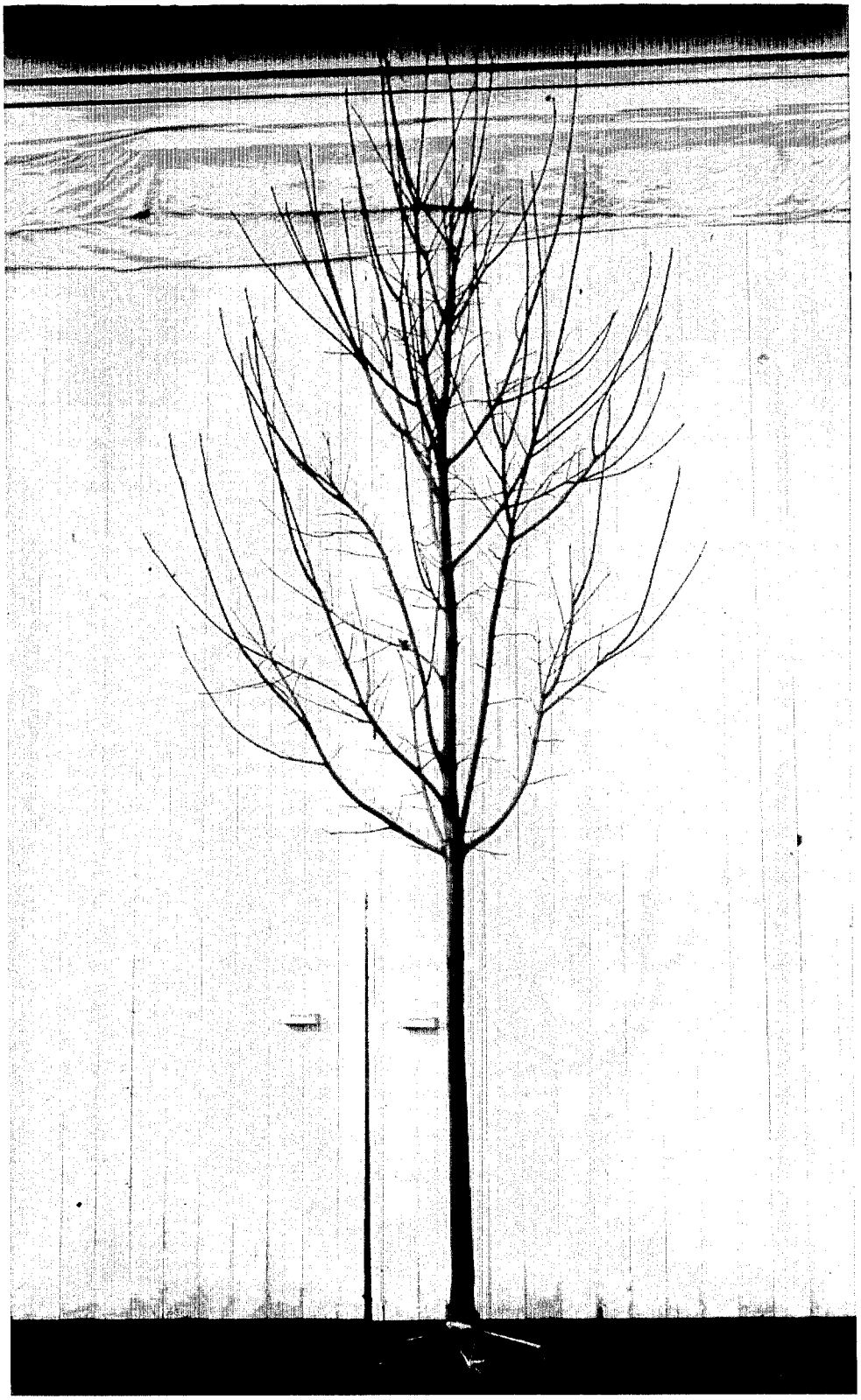
FIG. 3 is a photograph of my new variety as it appears without leaves.

The following is a detailed description of my new variety of sugar maple tree, the stated observations having been made on trees growing in nursery at Cambridge, N.Y., and for me at Fairview and Gresham, Oreg.

Origin: Seedling.

Parentage: Unknown.

Botanical name: Variant of *Acer saccharum.*

Form: Tree.

Shape: Upright with tight, dense, well-shaped, compact, ovoid crown.

Height: 2 to 2¾ inch caliper at 12 to 13 feet and extremely faster growing than patented varieties Green Mountain and Legacy in Moller's Nursery.

Trunk size: From ¾ to 1 inch each growing season.

Growth rate: Extremely fast for the species with excellent strength. After three growing seasons, the progeny averaged 2.31 inches after whip stage.

Bark:

*Color.*—Gray.

Branches: Numerous, stout, and all ascending uprightly.

*Angle of attachment.*—50°.

*Size.*—64 Inches in length of bottom branches, the middle branches extend about 40 inches and the top branches extend 24 inches. All are attached to a strong leader.

*Spacing.*—Varies from 4 inches to two feet. However, most of the branches are very close.

Leaves: Mature.

*Size.*—6½ Inches long; 7 inches wide. The leaf is extra large and the progeny are also showing large leaves.

*Form.*—Obicular, smooth, with sinuate teeth.

*Quantity.*—Dense. Crown — rounded ovoid.

*Color.*—Upper side: Dark green. R.H.S. 136C. Under side: Paler. R.H.S. 128B.

*Ribs and veins.*—Palmately veined.

*Winter buds.*—¼ Inch in average length, long and sharply pointed.

*Fall foliage color.*—R.H.S. 168.

Fruit: Has not fruited yet.

This variety resembles a sugar maple tree (*Acer saccharum*) and is clearly distinguished from other sugar maple trees by its extremely rapid growth habit in a stand growing under similar field conditions, its abundance of leaves, and its symmetrically ovoid shaped head not seen in other sugar maple trees at an early age, holding its distinguishing characteristics through propagation by budding and consistently producing heavily branched, uniform progeny with straight boles and a nicely shaped crown, and is further distinguished by being free from frost cracking and survival at 38° F. below zero with no cracking or sun scald.

I claim:

1. A new and distinct variety of sugar maple tree, substantially as herein shown and described, characterized by the unique combination of relatively fast and dense growth in comparison to most sugar maple trees, a symmetrically shaped ovoid crown, freedom from frost cracking and by being extremely hardy, surviving in 38° F. below zero with no splitting or sun scald problems, and having very large leaves.

* * * * *

UNITED STATES PATENT OFFICE
CERTIFICATE OF CORRECTION

PATENT NO. : Plant 5273
DATED : August 21, 1984
INVENTOR(S) : Roger L. Ashton

It is certified that error appears in the above-identified patent and that said Letters Patent are hereby corrected as shown below:

In column 1, second line from the bottom, change "Moller" to "McGill & Son".

Signed and Sealed this

*Twelfth* Day of *February 1985*

[SEAL]

*Attest:*

DONALD J. QUIGG

*Attesting Officer* *Acting Commissioner of Patents and Trademarks*

UNITED STATES PATENT AND TRADEMARK OFFICE

CERTIFICATE OF CORRECTION

PATENT NO. : Plant 5,273

DATED : August 21, 1984

INVENTOR(S) : Roger L. Ashton

It is certified that error appears in the above-identified patent and that said Letters Patent is hereby corrected as shown below:

On the title page item [54] should read:

SUGAR MAPLE NAMED FLAX MILL

Modify the Specification at Page 1, Col. 2, after line 37 to insert:

--The new variety of the present invention has been named the FLAX MILL variety, and is being marketed under the MAJESTY trademark.--

Signed and Sealed this

Twenty-seventh Day of September, 1994

*Attest:*

Bruce Lehman

BRUCE LEHMAN

*Attesting Officer*

*Commissioner of Patents and Trademarks*